(12) United States Patent
Andrysiak et al.

(10) Patent No.: US 6,843,779 B1
(45) Date of Patent: Jan. 18, 2005

(54) HEMODIALYSIS SYSTEM

(75) Inventors: Philip Andrysiak, Miami, FL (US); Gary Mishkin, Potomac, MD (US)

(73) Assignee: MiriMedical, LLC, Potomac, MD (US)

( * ) Notice: Subject to any disclaimer, the term of this patent is extended or adjusted under 35 U.S.C. 154(b) by 244 days.

(21) Appl. No.: 09/953,301

(22) Filed: Sep. 17, 2001

(51) Int. Cl.[7] .......................... A61M 37/00; C02F 1/44; C02F 9/00; B01D 63/00

(52) U.S. Cl. ..................... 604/5.01; 604/5.04; 210/646; 210/195.2; 210/321.71; 210/321.72

(58) Field of Search ...................... 604/4.01, 5.01–5.04, 604/65, 67; 422/44, 99, 101, 103; 210/645–47, 650–51, 739, 741, 767, 790, 85, 87–89, 97, 102, 143, 194, 195.1–195.2, 252, 255, 257.1–257.2, 259, 260, 321.6, 321.71–321.72, 321.75, 321.84

(56) References Cited

U.S. PATENT DOCUMENTS

| | | | |
|---|---|---|---|
| 4,229,299 A | * | 10/1980 | Savitz et al. .................. 210/85 |
| 5,660,722 A | * | 8/1997 | Nederlof ....................... 210/90 |
| 6,117,100 A | | 9/2000 | Powers et al. |
| 6,192,900 B1 | | 2/2001 | Arnal et al. |
| 6,406,631 B1 | * | 6/2002 | Collins et al. .............. 210/646 |

* cited by examiner

*Primary Examiner*—Patricia Bianco
(74) *Attorney, Agent, or Firm*—Browdy and Neimark, P.L.L.C.

(57) ABSTRACT

An apparatus and method for use in blood dialysis. The apparatus includes: two dialyzers each containing a semipermeable membrane that divides the dialyzer into a blood compartment and a dialysate compartment; a blood compartment connecting line connecting the blood compartments of the dialyzers together in series; blood connecting lines for connecting the blood compartments to the vascular system of a patient; a dialysate compartment connecting unit connecting the dialysate compartments of the dialyzers together in series; and dialysate connecting lines for connecting the dialysate compartments to a dialysis machine. The dialysate compartment connecting unit includes an adjustable flow varying device for controllably setting the rate of the flow of dialysate through the connecting unit.

6 Claims, 3 Drawing Sheets

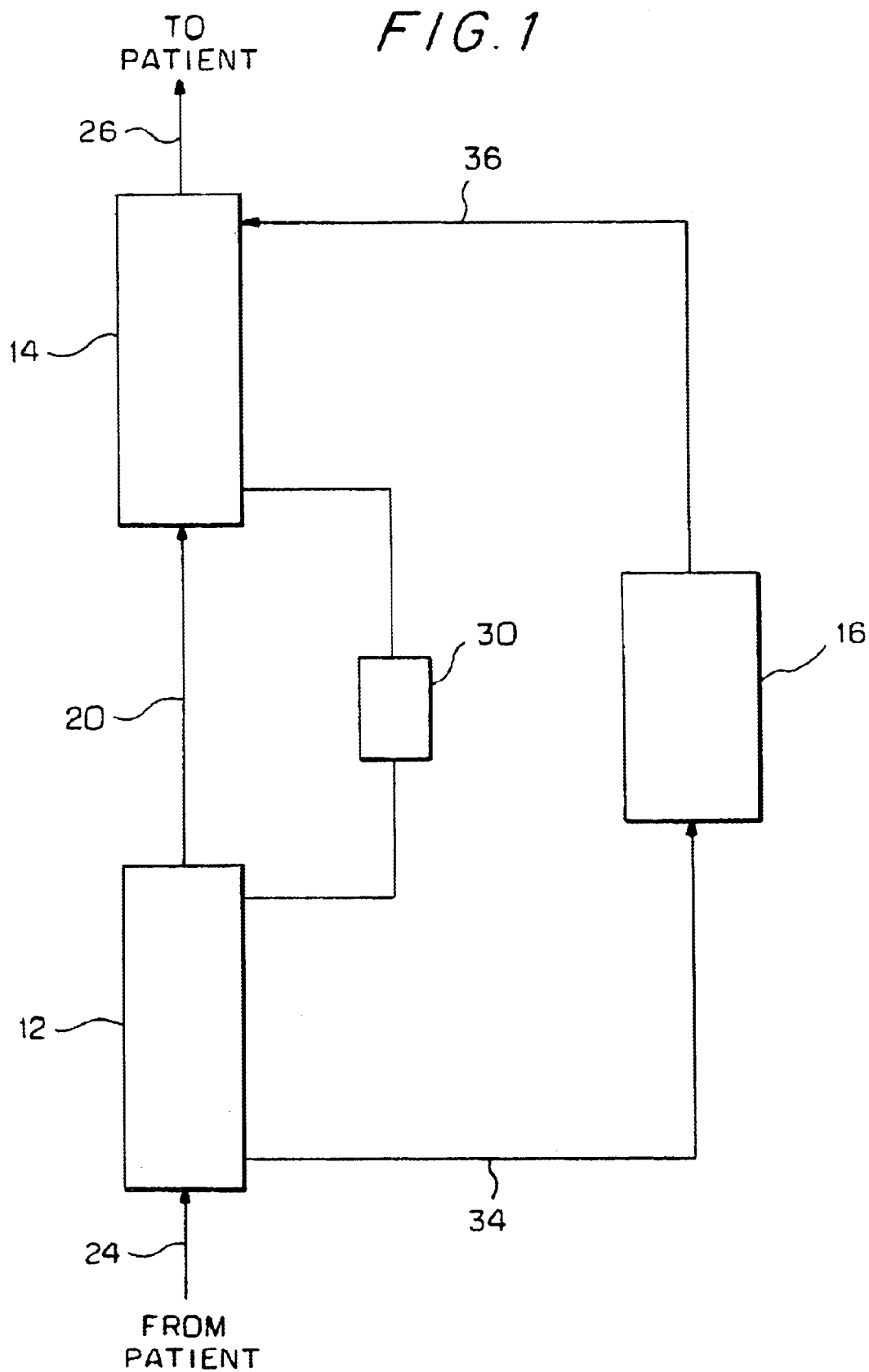

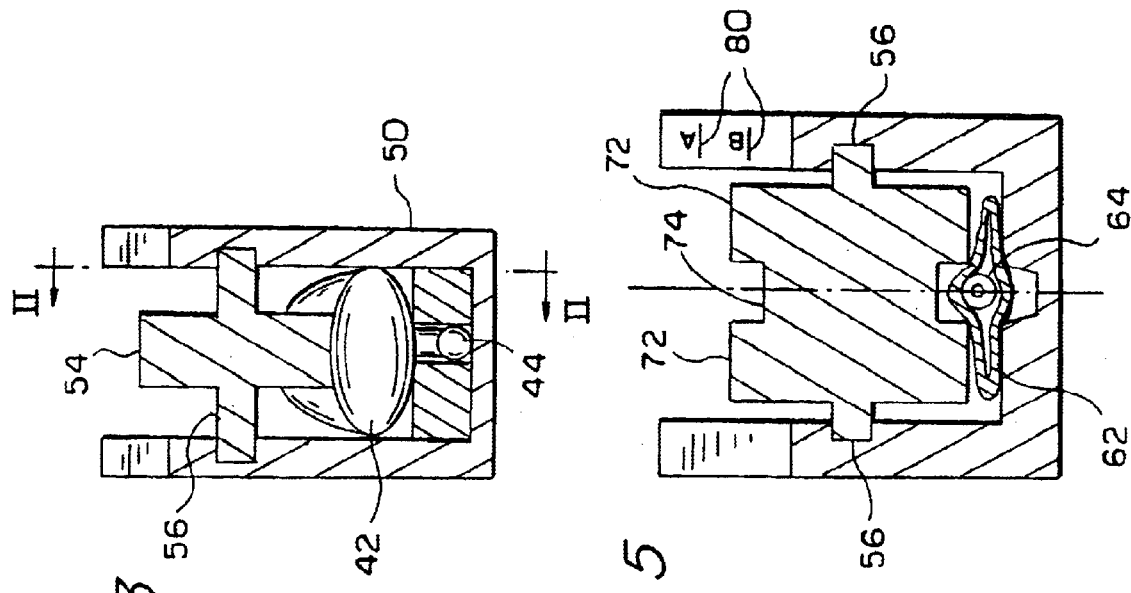
FIG.3
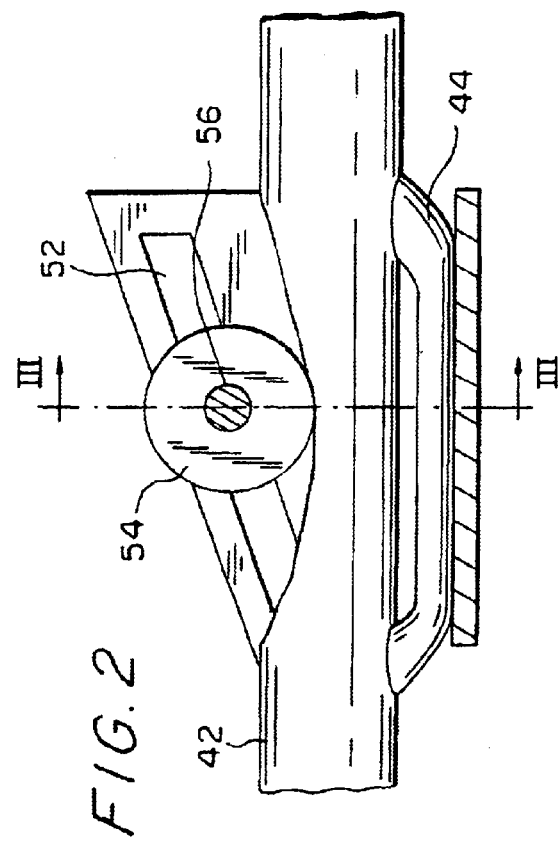
FIG.2
FIG.5
FIG.4

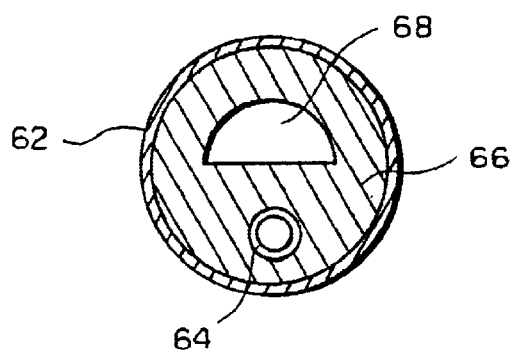
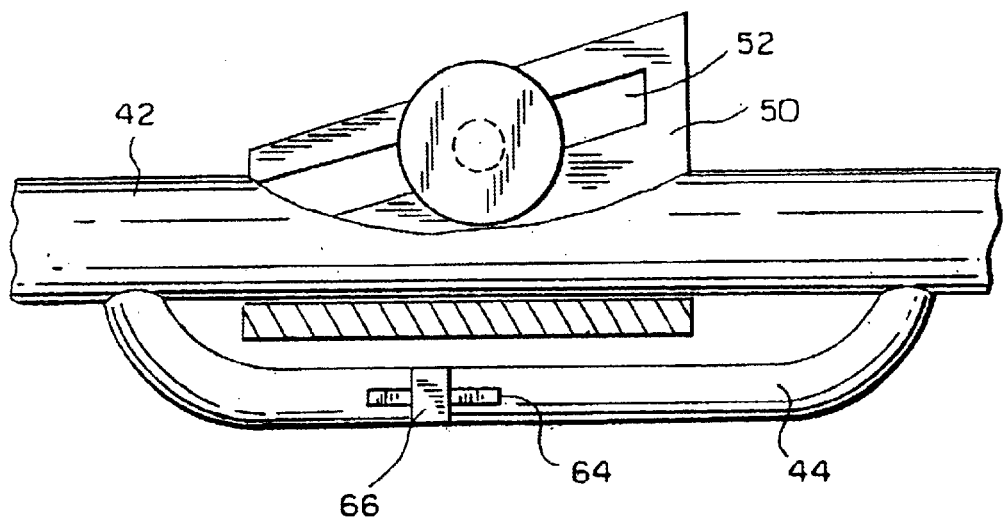
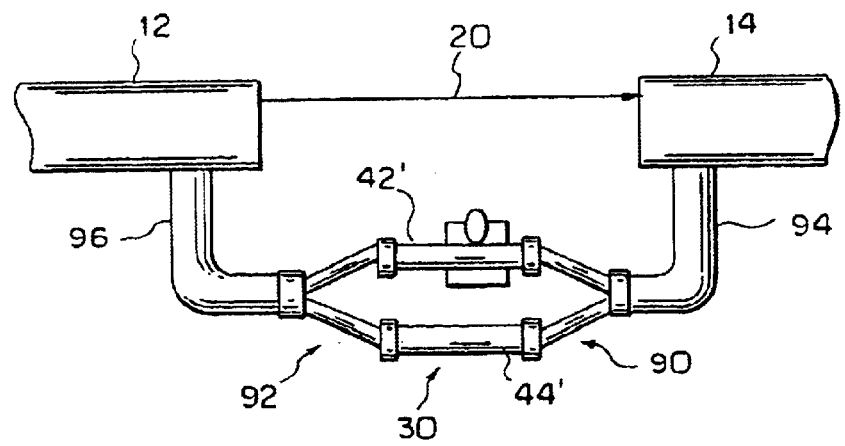

HEMODIALYSIS SYSTEM

BACKGROUND OF THE INVENTION

The present invention relates to hemodialysis for removing blood-borne uremic toxins and by-products of metabolism from the blood of patients suffering from renal failure.

This procedure is performed in dialysis apparatus generally composed of one or more dialyzers in which a blood compartment is separated from a dialysate compartment by a filter structure and a dialysis machine that controls the rate of flow and composition of the dialysate and monitors the dialysis procedure.

Apparatus of this type is available in a variety of forms. For example, the apparatus may be composed of two dialyzers whose respective compartments are connected in parallel or series. Each such form of construction has advantages and disadvantages. All known arrangements have certain drawbacks that adversely affect the quality and/or speed of a complete dialysis procedure.

A typical parallel arrangement is disclosed in U.S. Pat. No. 6,117,100.

Double high flux (DHF) dialysis is a known technique that uses two high flux dialyzers in series and a volumetric controlled dialysis machine. The dialysate flow path is altered in order to provide pressure differentials across each dialyzer, causing the first dialyzer to act as an ultrafilter while the second dialyzer performs infusion of substitution fluid by backfiltration. This treatment can advantageously be performed in newer machines that offer a sufficient calibration of the transmembrane pressure (TMP) gauge and arterial pressure gauge, a high blood pump speed, two dialysate filters to filter the dialysate fluid prior to entering the dialyzer and a high pressure of the incoming water.

DHF has also been referred to as high flux hemodiafiltration. This is because this treatment combines the enhanced convective removal associated with ultrafiltration with the diffusive removal associated with counter current dialysate. The two dialyzers, in series, double the effective surface area. For example, the dialysate flow may be set to 800 ml/min, with approximately 150 ml/min of this used for backfiltration, yielding a useful dialysate flow of 650 ml/min through the first dialyzer.

There are several limitations to the current application of DHF:

1) Patient selection. Patients, for known systems DHF, must have adequate vascular blood flow in order to provide extracorporeal blood flows of 650 ml/min. Most DHF patients have fistulas, however PTFE grafts can provide adequate blood flow. The known systems and procedures can not be used with patients who either do not want larger needles for blood access or do not have a blood access that provides a good enough flow to sustain a delivered flow of at least 550 ml/min.
2) Modification of equipment: As discussed previously, several modifications to existing equipment must be made in order to enable the delivery of DHF. These add risk to the treatment and liability to the clinic that alters the equipment. However, new machines are being produced which have wider TMP and arterial pressure ranges that permit the pressures achieved during DHF.
3) If lower blood flows (<550 ml/min) are used with the existing set up of DHF, there is an increased concern of dialyzer clotting as plasma water is ultrafiltered, thereby hemoconcentrating the blood in the first dialyzer. The current therapy requires full opening of the clamp at low blood flows, which reduces the ultrafiltration capability of the system.

BRIEF SUMMARY OF THE INVENTION

The present invention provides an improved dialysis apparatus and procedure that mitigate various drawbacks of the type described above.

For this purpose, the invention provides an apparatus for use in blood dialysis comprising:

first and second dialyzers each containing a semipermeable membrane that divides the dialyzer into a blood compartment and a dialysate compartment, the dialysate compartment of each dialyzer being connectable to a dialysis machine;

a blood compartment connecting line connecting the blood compartments of the dialyzers together in series;

blood connecting lines for connecting the blood compartments to the vascular system of a patient; and a dialysate compartment connecting unit connecting the dialysate compartments of the dialyzers together in series, wherein the dialysate compartment connecting unit comprises an adjustable flow varying device for controllably setting the rate of the flow of dialysate through the connecting unit, the device being constructed to progressively vary the dialysate flow rate through the connecting unit.

The invention also provides a method for performing dialysis on a patient with the apparatus described above, comprising:

connecting the dialysate compartments to a dialysis machine;

connecting the blood connecting lines to the vascular system of a patient;

placing the dialysis machine into operation; and setting the rate of flow of the dialysate by adjusting the flow varying device to establish a selected relative pressure in the dialyzers.

BRIEF DESCRIPTION OF THE DRAWINGS

FIG. 1 is a block diagram of a dialysis apparatus to which the present invention is applied.

FIG. 2 is a cross-sectional view taken along the line II—II of FIG. 3.

FIG. 3 is a cross-sectional view taken along line III—III of FIG. 2 of a first embodiment of a connecting device according to the invention.

FIGS. 4 and 5 are views similar to those of FIGS. 2 and 3, respectively, of a second embodiment of a connecting device according to the invention.

FIG. 6 is a cross-sectional view taken along line VI—VI of FIG. 4.

FIG. 7 shows another embodiment of a connecting device according to the invention.

FIG. 8 is a simplified pictorial view showing another embodiment of a connecting device according to the invention.

DETAILED DESCRIPTION OF THE INVENTION

FIG. 1 illustrates the type of dialysis apparatus to which the present invention is applied. This apparatus is composed essentially of two dialyzers 12 and 14 and a dialysis machine 16, all of which are of conventional type. An exemplary dialyzer that may be used in apparatus according to the invention in disclosed in U.S. Pat. No. 6,117,100.

Each dialyzer 12, 14 is formed to contain a blood compartment and a dialysate compartment (not shown in detail). These compartments are separated from one another by semipermeable membranes having appropriate selective filtering properties.

In apparatus intended to achieve the results of the present invention, the blood flow compartments of dialyzers 12 and 14 are connected together in series, as are the dialysate compartments. Specifically, the dialyzer compartments of dialyzers 12 and 14 are connected together in series by a blood compartment connecting line 20. Blood connecting lines 24 and 26 are provided to couple the system to the circulatory system of the patient so that blood will flow from the patient via line 24 and be returned to the patient via line 26.

The dialysate compartments of the two dialyzers 12 and 14 are connected together in series by a dialysate compartment connecting unit 30 and the series arrangement of the two dialysate compartments is-connected to dialysis machine 16 by dialysate connecting lines 34 and 36. Specifically, lines 34 and 36 are connected so that dialysate is pumped from machine 16 through line 36 and is returned to machine 16 through line 34. Thus, in dialyzers 12 and 14 dialysate flows in counter current to the flow of blood.

The performance of the disclosed apparatus, i.e. the effectiveness of the blood cleaning operation, depends, inter alia, on the pressure differential across the membrane separating each blood compartment from the dialysate compartment in the associated dialyzer 12, 14. Machine 16 has a pump mechanism, known as a volumetric control, that insures that the quantity of dialysate entering the dialyzers is equal to that leaving the dialyzers, plus a defined quantity of excess fluid. The excess fluid is to be removed from the patient and represents the quantity of fluid accumulated in the patient's body since the previous dialysis.

According to the present invention, an improved control of these pressure differentials is achieved by constructing unit 30 to allow a progressive, accurately controllable adjustment of the flow resistance provided by that unit, thereby allowing an accurate and progressive adjustment of the relation between the dialysate pressures in dialyzers 12 and 14.

A first embodiment of a dialysate compartment connecting unit is shown in FIGS. 2 and 3, FIG. 3 being a cross-sectional view taken along line III—III of FIG. 2 and FIG. 2 being a cross-sectional view taken along the line II—II of FIG. 3. This unit includes a primary flexible tube 42 that is connected between the dialysate compartments of dialyzers 12 and 14 and provides a primary dialysate flow path. A second tube 44 is connected in parallel with a section of tube 42 and is provided to define a minimum dialysate flow path, as will be explained in detail below. The provision of a minimum flow path having a fixed flow resistance serves to prevent the triggering of a machine alarm and clotting of the blood flow circuit of the dialyzers due to excessive ultrafiltration.

Both tubes 42 and 44 extends through a roller clamp device that is composed of a generally U-shaped support member 50 having side walls provided internally with elongated grooves, or slots, 52 and a roller 54 having axial members 56 that are held in grooves 52. As illustrated, grooves 52 are inclined relative to the longitudinal axis of tube 42 so that when roller 54 is rolled along groves 54, which is done manually, tube 42 will be progressively constricted. By proper dimensioning of the diameter of roller 54 and of the location of and inclination of grooves 52, movement of roller 54 along grooves 52 can cause the cross-section of tube 42 to progress from a maximum area, when tube 42 has a round cross section, to a minimum, and even zero, area, when roller 54 is at the lower end of grooves 52. It will be noted that even if tube 42 is fully constricted so that there is no flow of dialysate therethrough, tube 44 will continue to provide the minimum dialysate flow path to assure continued safe operation of the apparatus.

Typically, tube 42 will be made of a flexibly resilient plastic that offers a certain resistance to constriction when roller 54 is advanced downwardly along grooves 52. This resistance will act to press axial members 56 against the upper edges of grooves 52, with the result that roller 54 will remain in whatever position along grooves 52 that it is placed by the operator. Thus, it is possible to progressively vary the internal cross-sectional area of tube 42 and, correspondingly, to vary the flow resistance offered by unit 30 and the rate of dialysate flow through the system. As the flow resistance of unit 30 is increased, the pressure at the outlet end of the dialysate compartment of dialyzer 14 will increase and that at the inlet end of the dialysate compartment of dialyzer 12 will decrease. This will affect the exchange operation being carried out in each dialyzer. Specifically, as the flow resistance presented by unit 30 is increased, the rate of ultrafiltration in dialyzer 12 and the rate of backfiltration in dialyzer 14 both increase.

A second embodiment of a unit 30 according to the invention is illustrated in FIGS. 4 and 5, which contain views similar to those of FIGS. 2 and 3, respectively.

In the embodiment shown in FIGS. 4 and 5, there is only one tube 62, which is a flexible tube like tube 42. Tube 62 contains a hollow restrictor rod 64 that will provide a minimum dialysate flow path when tube 62 has been constricted to a maximum extent. Rod 64 is secured in tube 62 by a support element 66 provided with at least one fluid flow passage 68.

This embodiment includes a roller having, in addition to axial members 56, two lateral parts 72 spaced from one another along the axis of rotation of the roller, and particularly along the axis defined by members 56, and a central part 74 that has a smaller diameter than lateral parts 72 and is interposed between parts 72. As is readily apparent from the view of FIG. 5, parts 72 and 74 cooperate to enable tube 62 to be substantially completely flattened without imposing any substantial deformation force on rod 64. Thus, when the roller is at the lowest end of grooves 52, imposing a maximum deformation on tube 62, dialysate flow can continue through rod 64 to produce the same result as flow through tube 44 in the embodiment shown in FIGS. 2 and 3.

According to a further feature of the invention, the roller clamp can be provided with visible markers, or indicia, 80, as shown in FIG. 5. Such indicia can also be provided on other roller clamp housings according to the invention, such as housing 50 shown in FIGS. 2 and 3. These indicia will provide at least a rough indication of the degree of constriction being imposed on tube 42 or 62. However, it is preferred that the precise positioning of the roller along grooves 52 be determined on the basis of readings provided by indicators associated with machine 16.

FIG. 6 is a cross-sectional view taken along line VI—VI of FIG. 4, showing the details of support element 66 and rod 64.

According to a further embodiment of the invention, restrictor rod 64 and its associated support element 66 could be installed in tube 44 of the embodiment shown in FIGS. 2 and 3 in order to reduce the cross-sectional area of the minimum dialysate flow path.

Another embodiment of a roller clamp assembly according to the invention is shown in FIG. 7, which is a view similar to that of FIGS. 2 and 4. This embodiment differs from that shown in FIGS. 2 and 3 essentially in that housing 50 surrounds only flexible tube 42. This enables housing 50 to be given a simpler structure and ensures that the action of the roller clamp will not affect the cross-sectional area of tube 44. Here again, rod 64 and its associated support elements 66 can optionally be included in tube 44.

A further embodiment shown in FIG. 8, is equipped with a dialysate compartment connecting unit 30 that includes two Y connectors 90 and 92. Y connector 90 connects a single tube 94 to two parallel tubes 42' and 44'. Tube 94 is connected to the outlet end of the dialysate compartment of dialyzer 14. Tube 42' is a standard tube of a compressible material and is associated with a roller clamp according to the invention that is movable to completely open, partially close, or fully close the flow path through this tube. The roller clamp can be identical to that shown in FIG. 7.

Tube 44' is not compressed and may have a flow restrictor installed therein, such as the flow restrictor shown in FIGS. 6 and 7. However, the flow restrictor can be any small diameter device inserted into the flow path so that all fluid entering tube 44' must pass through the restrictor. The restrictor could, for example, be a 2 cm long plastic cylinder with a 2 mm inner diameter that is inserted into the flow path of tube 44' so that all fluid entering tube 44' must pass through the cylinder.

When the clamp on tube 42' is fully or partially open, fluid passes through both tubes, divided according to the respective flow resistances of the tubes. Downstream of the restrictor and clamp, the two tubes are again united by the second Y connector 92, which is attached to the inlet end of the dialysate compartment of dialyzer 12 by a single tube 96.

As in the operation of the other embodiments of the invention, when the clamp is fully closed, all of the dialysate flows through tube 44'. The dialysate pressure upstream of unit 30, in the dialysate compartment of dialyzer 14, is then very high, while the pressure downstream of unit 30, in the dialysate compartment of dialyzer 12, is very low. This permits fluid ultrafiltration from the blood to the dialysate in dialyzer 12 and backfiltration of dialysate to the blood in dialyzer 14.

The dialysate flow through the restrictor provides the pressure differential for large ultrafiltration in dialyzer 12, yielding additional convective removal of middle weight molecules. A typical middle weight molecule is β2 microglobulin which is approximately 11,800 daltons. The quantity of fluid ultrafiltered in dialyzer 12 is compensated for by backfiltration of dialysate in dialyzer 14. The volumetric control in the dialysis machine will ensure the balance of fluid, accounting for proper removal of fluid gained by the patient since the preceding dialysis.

In all of the embodiments of the invention, the roller clamp enables the user to adjust the flow through the first tube by evaluating the TMP levels. As the roller is rolled, it gradually reduces the flow through the associated tube. The reduction of flow through one tube results in an increase in flow to the second tube, which may be provided with the restrictor. This will alter the pressures as discussed above and enhance ultrafiltration and convective removal of middle molecular weight solutes (i.e. β2 microglobulin). When the TMP approaches the alarm limits, no further constriction, via the roller clamp, should be made.

Embodiments of the invention can be applied to at least certain existing dialysis equipment, although it may be desirable to provide different sized dialyzers with different ultrafiltration capabilities and lower dialyzer blood flows. Since it will be possible to variably control the rate of filtration and backfiltration by adjusting the roller clamp, it will be possible to apply this treatment to a larger number of patients with a wide range of attainable blood flows. This will also provide a method for individualizing the treatment for each patient's needs.

A dialysate compartment connecting unit according to the invention will be used in the following manner:

1. Two dialyzers will be connected together and to a dialysis machine as shown in FIG. 1, and will be connected to the patient.
2. The roller clamp will remain fully open as the treatment is initiated.
3. As the blood flow reaches a prescribed level, the roller clamp will be slowly adjusted to increase the filtration and back filtration.
4. The roller clamp should be adjusted so that pressure sensors on the dialysis machine do not alarm. The clinic may decide to shift the calibration of the sensors in order to increase the possible filtration rate without machine alarms. Alternatively, the clinic may decide to maximize the fraction of plasma water that passes through the dialysis membrane to no greater than 25–33% of the blood flow through the machine dependent on hematocrit level, or 50% filtration of the plasma water.
5. The rate of ultrafiltration can be approximated as a product of the Kuf and the transmembrane pressure (TMP) in the dialyzer. Values for these characteristics are commonly found in the medical literature and in the dialyzer manufacturer's product literature. Kuf is the coefficient of ultrafiltration with the units: cc/hour/mmHg. TMP is the pressure difference between the blood side and the dialysate side of the dialyzer at given blood flows.
6. The roller clamp can be adjusted throughout the treatment if necessary as the hematocrit increases as plasma water (patient weight gain) is removed and the blood becomes more viscous, reducing filtration rate and increasing pressures.
7. After treatment, the roller clamp should be fully opened and the blood flow reduced as the treatment is terminated and the patient is disconnected from the dialysis machine.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An apparatus for use in blood dialysis comprising:
   first and second dialyzers each containing a semipermeable membrane that divides the dialyzer into a blood compartment and a dialysate compartment, the dialysate compartment of each dialyzer being connectable to a dialysis machine;
   a blood compartment connecting line connecting the blood compartments of said dialyzers together in series;
   blood connecting lines for connecting said blood compartments to the vascular system of a patient; and
   a dialysate compartment connecting unit connecting the dialysate compartments of said dialyzers together in series, wherein said dialysate compartment connecting unit comprises an adjustable flow varying device for controllably setting the rate of the flow of dialysate through said connecting unit, said device being constructed to progressively vary the dialysate flow rate through said connecting unit, said dialysate compartment connecting unit comprises a flexible tube and said adjustable flow varying device comprises a roller clamp composed of a roller that is movable along a path to progressively constrict said tube, and said dialysate compartment connecting unit further comprises a hollow rod installed within, and having a smaller diameter than, said flexible tube, said roller clamp being operative to not deform said hollow rod so that said hollow rod defines a minimum dialysate flow path when said flexible tube is fully constricted.

2. The apparatus of claim 1 wherein said hollow rod is substantially rigid.

3. The apparatus of claim 1 wherein: said roller has two lateral cylindrical parts for engaging said flexible tube, said lateral cylindrical parts being spaced from one another along the axis of said roller; and said hollow rod is disposed in a region between said lateral cylindrical parts.

4. An apparatus for use in blood dialysis comprising:

first and second dialyzers each containing a semipermeable membrane that divides the dialyzer into a blood compartment and a dialysate compartment, the dialysate compartment of each dialyzer being connectable to a dialysis machine;

a blood compartment connecting line connecting the blood compartments of said dialyzers together in series;

blood connecting lines for connecting said blood compartments to the vascular system of a patient; and a dialysate compartment connecting unit connecting the dialysate compartments of said dialyzers together in series, wherein said dialysate compartment connecting unit comprises an adjustable flow varying device for controllably setting the rate of the flow of dialysate through said connecting unit, said device being constructed to progressively vary the dialysate flow rate through said connecting unit, said dialysate compartment connecting unit comprises a flexible tube and said adjustable flow varying device comprises a roller clamp composed of a roller that is movable along a path to progressively constrict said tube, and said dialysate compartment connecting unit further comprises a second tube connected in parallel with said flexible tube and disposed to not be deformed by said roller clamp to define a minimum dialysate flow path when said flexible tube is fully constricted.

5. A method for performing dialysis on a patient with the apparatus according to claim 1, comprising:

connecting the dialysate compartments to a dialysis machine;

connecting the blood connecting lines to the vascular system of a patient;

placing the dialysis machine into operation; and setting the rate of flow of the dialysate by adjusting the flow varying device to establish a selected relative pressure in the dialyzers.

6. The method of claim 5 wherein said step of setting comprises adjusting the flow varying device during a dialysis procedure.

\* \* \* \* \*